US008476243B2

(12) United States Patent
Kaspar et al.

(10) Patent No.: US 8,476,243 B2
(45) Date of Patent: Jul. 2, 2013

(54) METHODS AND COMPOSITIONS FOR TREATING KERATIN HYPERPROLIFERATIVE DISORDERS

(75) Inventors: Roger Louis Kaspar, Santa Cruz, CA (US); Robyn Patricia Hickerson, Santa Cruz, CA (US)

(73) Assignee: Transderm, Inc., Salt Lake City, UT (US)

(*) Notice: Subject to any disclaimer, the term of this patent is extended or adjusted under 35 U.S.C. 154(b) by 1670 days.

(21) Appl. No.: 11/618,138

(22) Filed: Dec. 29, 2006

(65) Prior Publication Data
US 2009/0181908 A1 Jul. 16, 2009

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC ........................................ 514/44 A; 536/24.5

(58) Field of Classification Search
USPC .......................................................... 514/44
See application file for complete search history.

(56) References Cited

U.S. PATENT DOCUMENTS

| | | | |
|---|---|---|---|
| 5,994,081 A | 11/1999 | Tang et al. | |
| 6,221,843 B1 | 4/2001 | Tang et al. | |
| 2002/0086356 A1 | 7/2002 | Tuschl et al. | |
| 2003/0170630 A1 | 9/2003 | Alsobrook et al. | |
| 2004/0087480 A1 | 5/2004 | Rane et al. | |
| 2007/0031844 A1 | 2/2007 | Khvorova et al. | |

FOREIGN PATENT DOCUMENTS

| | | |
|---|---|---|
| EP | 0 703 985 | 10/2003 |
| WO | WO 00/10516 | 3/2000 |
| WO | WO 2005/091891 A2 | 10/2005 |

OTHER PUBLICATIONS

Hickerson et al. (Ann. N.Y. Acad. Sci., 2006 vol. 1082:56-61). siRNA-mediated selective inhibition of mutant keratin mRNAs responsible for skin disorder pachyonychia congenita.*
www.rnai.news.com pp. 4 and 5 (published Sep. 30, 2005). RNAi startup believes siRNAs can treat extremely rare skin disorder.*
Scherer et al., Approaches for the Sequence-specific knockdown of mRNA, Nature Biotechnology, 2003, vol. 21, No. 12, Dec. 2003. p. 1457-1465.
Mahato et al., Modulation of gene expression by antisense and antigene oligodeoxynucleotides and small interfering RNA, Expert Opinion on Drug Delivery, Jan. 2005, vol. 2, No. 1, pp. 3-28.
Macron, Doug, RNAi Startup Believes siRNAs Can Treat Extremely Rare Skin Disorders (online).pp. 4-5, 2005, (retrieved on May 7, 2008), Retrieved from the Internet:URL:http://www.rnainews.com.
Reynolds et al., Rational siRNA design for RNA interference. Nature Biotech vol. 22 No. 3 Mar. 2004 pp. 326-330.
Terrinoni et al., Novel and Recurrent Mutations in the Genes Encoding Keratins K6a, K16 and K17 in 13 Cases of Pachyonychia Congenita. Investigational Dermatology 117: pp. 1391-1396, 2001.
Smith et al., A Mutation in Human Keratin K6b produces a phenocopy of the K17 disorder pachyonychia congenita type 2. Human Molecular Genetics 7: pp. 1143-1148. 1998.

(Continued)

*Primary Examiner* — Terra Cotta Gibbs
(74) *Attorney, Agent, or Firm* — Thorpe North & Western LLP

(57) ABSTRACT

A method for keratin hyperproliferation disorders such as corns, calluses, or keratosis pilaris (KP) by administering to a subject experiencing the disorder a therapeutically effective amount of an RNA sequence which inhibits expression of a gene encoding for a keratin selected from the group consisting of K6a, K6b, K16, K17, and combinations thereof.

21 Claims, 8 Drawing Sheets

Keratosis Pilaris Lesions: Case 1

Negative Control — K17
K16 — K6

OTHER PUBLICATIONS

Lin et al., Identification of Sporadic Mutations in the helix initiation motif of keratin 6 in two pachyonychia congenita patients: further evidence for a mutational hot spot. Exp Dermatol 1998/1999 pp. 115-119.

Mahajan et al., Pachyonychia congenita-like nail changes treated successfully with a combination of vitamins A and E: A case report. Retrieved on Jun. 11 2008; vol. 69 Issue 5 pp. 338-339. http://www.ijdvl.com/article.asp?issn=0378-6323;year=2003;volume69;issue=5;spage=338; . . . .

Soutschek et al., Therapeutic silencing of an endogenous gene by systemic administration of modified siRNA's. Nature 432; pp. 173-178. 2004.

McLean et al., Keratin 16 and keratin 17 mutations cause pachyonychia congenita. Nature Genetics, vol. 9, Mar. 1995.

IPPC 2004 meeting, Feb. 2004, (retrieved on May 8, 2008), Retrieved from the Internet<URL: http://www.pachyonychia1.org/IPCC/IPCC.program.AtaGlanCe-2004.pdf>.

Hickerson et al., SiRNA-mediated selective inhibition of mutant keratin mRNAs responsible for the skin disorder pachyyonychia congenita. Ann N Y Acad Sci. Oct. 2006; 1082: 56-61.

NCBI GenBank Accession No. BC014152 2345 bp mRNA linear PRI Jul. 24, 2006 Homo sapiens keratin 6A, mRNA (cDNA clone MGC:20671 Image:3639270), complete CDs. See nucleotide sequences.

NCBI GenBank Accession No. NM_005555 2331 bp mRNA linear PRI Dec. 20, 2006 Definition Homo sapiens keratin 6B (KRT6B), mRNA. See Nucleotide sequences.

NCBI GenBank Accession No. NM_005557 1688 bp mRNA linear PRI Nov. 17, 2006 Definition Homo sapiens keratin 16 (focal non-epidermolytic palmoplantar keratoderma) (KRT16), mRNA. See the nucleotide sequences.

NCBI GenBank Accession No. BC 072019 1514 bp mRNA linear PRI Jul. 15, 2006 Definition Homo sapiens keratin 17, mRNA (cDNA clone MGC:88731 Image:5442690), complete cds. See nucleotide sequences.

Lewin, Alfred S., Gene therapy for autosomal dominant disorders of keratin. J Investig Dermatol Symp Proc. Oct. 2005; 10(1): 47-61.

Smith FJ et al., A Mutation in human keratin K6b produces a phenocopy of the K17 disorder pachyonychia congenita type 2. Hum Mol Genet. Jul. 1998; 7(7):1143-1148.

Corden Ld et al., Human keratin diseases: hereditary fragility of specificepithelial tissues. Exp Dermatol. Dec. 1996; 5(6) 297-307.

Tyner AL et al., Evidence for posttranscriptional regulation of the keratins expressed during hyperproliferation and malignant transformation in human epidermis. J Cell Biol. Nov. 1986; 103 (5):1945-1955.

Jang Si et al., Characterization of human epiplakin: RNAi-mediated epiplakin depletion leads to the disruption of keratin and vimentin IF networks. J Cell Sci. Feb. 15, 2005; 118(pt 4): 781-793. Epub Jan. 25, 2005.

* cited by examiner

FIGURE 1A
Keratosis Pilaris Lesions: Case 1
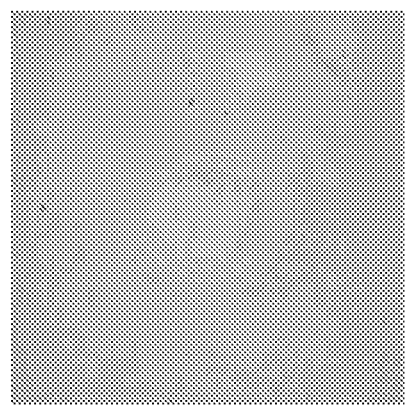
Negative Control
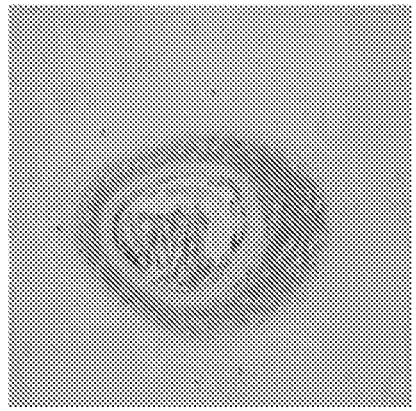
K17
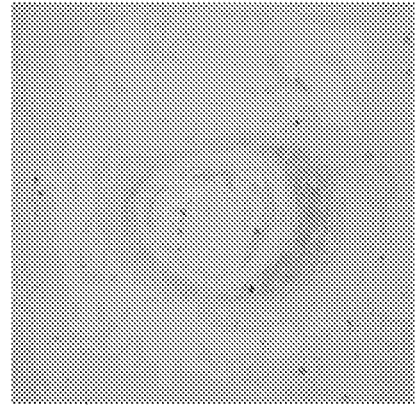
K16
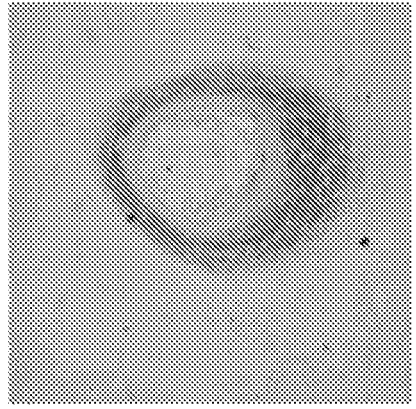
K6

FIGURE 1B
Keratosis Pilaris Lesions: Case 2
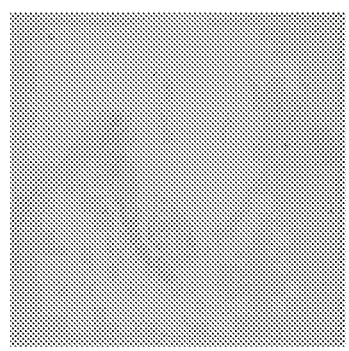
Negative Control
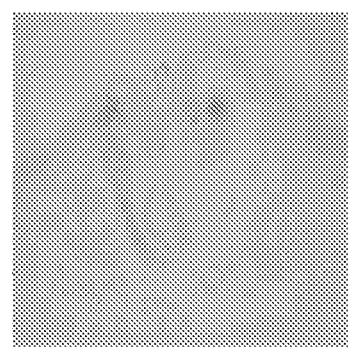
K16
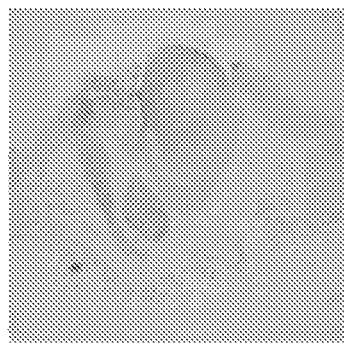
K6
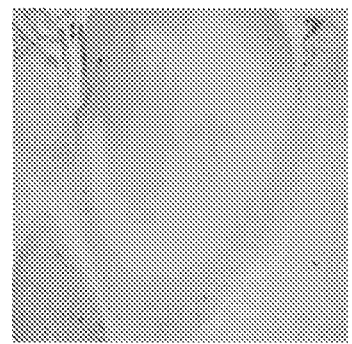
K6 closeup FIGURE 1C
Keratosis Pilaris Lesions: Case 3
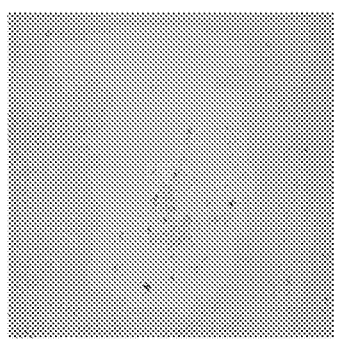
Negative Control
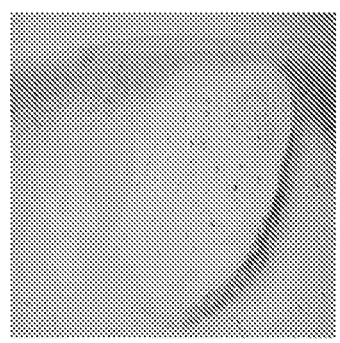
K17
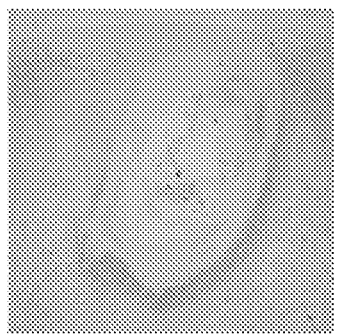
K16
K6

FIGURE 1D
Eccrine Glands
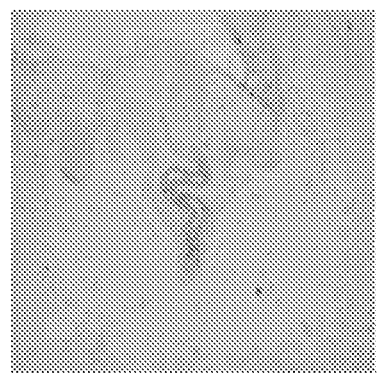
K16
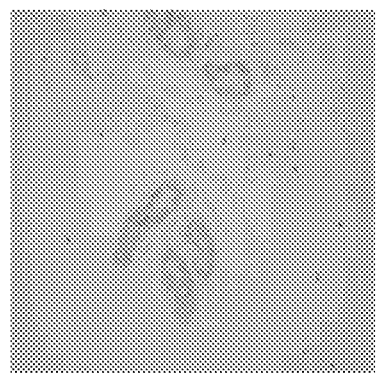
K6
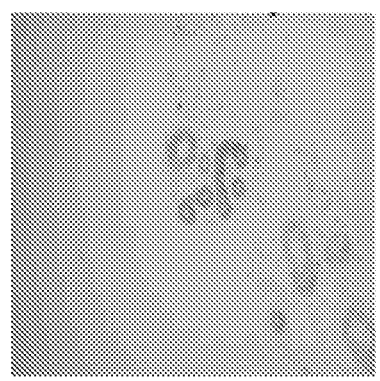
K16
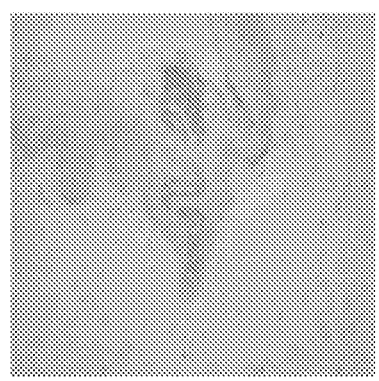
K17

FIGURE 3

A.
```
K6A WT      5' AACAGATCAAGACCCTCAACAACAAGTTTGCCT    SEQ. ID NO. 110
K6A C513A   5' AACAGATCAAGACCCTCAAAAACAAGTTTGCCT    SEQ. ID NO. 111

K6a_513a.4  (CON,12) GAUCAAGACCCUCAAaAACUU    SEQ. ID NO: 102
K6a_513c.4  (WT.4)   GAUCAAGACCCUCAAcAACUU    SEQ. ID NO: 103
K6a_513g.4           GAUCAAGACCCUCAAgAACUU    SEQ. ID NO: 104
K6a_513u.4           GAUCAAGACCCUCAAuAACUU    SEQ. ID NO: 105

K6a_513a.12 (CON,12)          CCCUCAAaAACAAGUUUGCUU    SEQ. ID NO: 106
K6a_513c.12 (WT.12)           CCCUCAAcAACAAGUUUGCUU    SEQ. ID NO: 107
K6a_513g.12                   CCCUCAAgAACAAGUUUGCUU    SEQ. ID NO: 108
K6a_513u.12                   CCCUCAAuAACAAGUUUGCUU    SEQ. ID NO: 109
```

B. 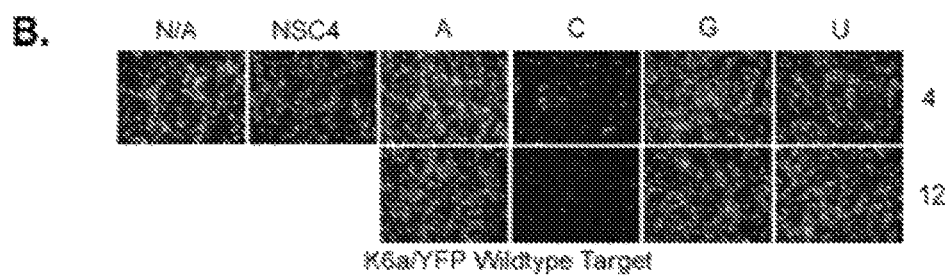
K6a/YFP Wildtype Target

C. 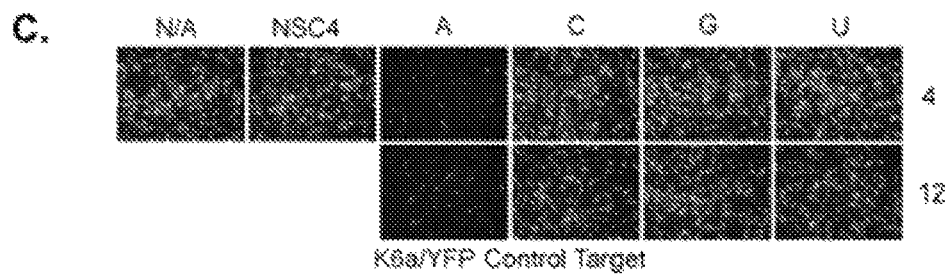
K6a/YFP Control Target

SEQUENCE LISTING

<160> NUMBER OF SEQ ID NOS: 111

<210> SEQ ID NO 1
<211> LENGTH: 21
<212> TYPE: RNA
<213> ORGANISM: Artificial
<220> FEATURE:
<223> OTHER INFORMATION: Synthetic

<400> SEQUENCE: 1
caagcgcaca gcagcagagu u                                              21

<210> SEQ ID NO 2
<211> LENGTH: 21
<212> TYPE: RNA
<213> ORGANISM: Artificial
<220> FEATURE:
<223> OTHER INFORMATION: synthetic

<400> SEQUENCE: 2
cucugcugcu gugcgcuugu u                                              21

<210> SEQ ID NO 3
<211> LENGTH: 21
<212> TYPE: RNA
<213> ORGANISM: Artificial
<220> FEATURE:
<223> OTHER INFORMATION: synthetic

<400> SEQUENCE: 3
ggauguggau gcugccuacu u                                              21

<210> SEQ ID NO 4
<211> LENGTH: 21
<212> TYPE: RNA
<213> ORGANISM: Artificial
<220> FEATURE:
<223> OTHER INFORMATION: synthetic

<400> SEQUENCE: 4
guaggcagca uccacauccu u                                              21

<210> SEQ ID NO 5
<211> LENGTH: 21
<212> TYPE: RNA
<213> ORGANISM: Artificial
<220> FEATURE:
<223> OTHER INFORMATION: synthetic

<400> SEQUENCE: 5
gaagcagugc gccaaccugu u                                              21

<210> SEQ ID NO 6
<211> LENGTH: 21
<212> TYPE: RNA
<213> ORGANISM: Artificial
<220> FEATURE:
<223> OTHER INFORMATION: synthetic

<400> SEQUENCE: 6
cagguuggcg cacugcuucu u                                              21

```
<210> SEQ ID NO 7
<211> LENGTH: 21
<212> TYPE: RNA
<213> ORGANISM: Artificial
<220> FEATURE:
<223> OTHER INFORMATION: synthetic

<400> SEQUENCE: 7
gucaacaucu cugguggcu u                                               21

<210> SEQ ID NO 8
<211> LENGTH: 21
<212> TYPE: RNA
<213> ORGANISM: Artificial
<220> FEATURE:
<223> OTHER INFORMATION: synthetic

<400> SEQUENCE: 8
gcaccacaga gauguugacu u                                              21

<210> SEQ ID NO 9
<211> LENGTH: 21
<212> TYPE: RNA
<213> ORGANISM: Artificial
<220> FEATURE:
<223> OTHER INFORMATION: synthetic

<400> SEQUENCE: 9
caucucugug gugcaguccu u                                              21

<210> SEQ ID NO 10
<211> LENGTH: 21
<212> TYPE: RNA
<213> ORGANISM: Artificial
<220> FEATURE:
<223> OTHER INFORMATION: synthetic

<400> SEQUENCE: 10
ggacugcacc acagagaugu u                                              21

<210> SEQ ID NO 11
<211> LENGTH: 21
<212> TYPE: RNA
<213> ORGANISM: Artificial
<220> FEATURE:
<223> OTHER INFORMATION: synthetic

<400> SEQUENCE: 11
gcagcuacuc cuauggcagu u                                              21

<210> SEQ ID NO 12
<211> LENGTH: 21
<212> TYPE: RNA
<213> ORGANISM: Artificial
<220> FEATURE:
<223> OTHER INFORMATION: synthetic

<400> SEQUENCE: 12
cugccauagg aguagcugcu u                                              21

<210> SEQ ID NO 13
<211> LENGTH: 21
<212> TYPE: RNA
<213> ORGANISM: Artificial
<220> FEATURE:
<223> OTHER INFORMATION: synthetic
```

```
<400> SEQUENCE: 13
ucaccacugg agcuucacuu u                                              21

<210> SEQ ID NO 14
<211> LENGTH: 21
<212> TYPE: RNA
<213> ORGANISM: Artificial
<220> FEATURE:
<223> OTHER INFORMATION: synthetic

<400> SEQUENCE: 14
agugaagcuc caguggugau u                                              21

<210> SEQ ID NO 15
<211> LENGTH: 22
<212> TYPE: RNA
<213> ORGANISM: Artificial
<220> FEATURE:
<223> OTHER INFORMATION: synthetic

<400> SEQUENCE: 15
gcacaaguga cuaguccuau uu                                             22

<210> SEQ ID NO 16
<211> LENGTH: 22
<212> TYPE: RNA
<213> ORGANISM: Artificial
<220> FEATURE:
<223> OTHER INFORMATION: synthetic

<400> SEQUENCE: 16
auaggacuag ucacuugugc uu                                             22

<210> SEQ ID NO 17
<211> LENGTH: 21
<212> TYPE: RNA
<213> ORGANISM: Artificial
<220> FEATURE:
<223> OTHER INFORMATION: synthetic

<400> SEQUENCE: 17
gugacuaguc cuaugauguu u                                              21

<210> SEQ ID NO 18
<211> LENGTH: 21
<212> TYPE: RNA
<213> ORGANISM: Artificial
<220> FEATURE:
<223> OTHER INFORMATION: synthetic

<400> SEQUENCE: 18
acaucauagg acuagucacu u                                              21

<210> SEQ ID NO 19
<211> LENGTH: 21
<212> TYPE: RNA
<213> ORGANISM: Artificial
<220> FEATURE:
<223> OTHER INFORMATION: synthetic

<400> SEQUENCE: 19
gcuucucucu cucucuauau u                                              21
```

```
<210> SEQ ID NO 20
<211> LENGTH: 21
<212> TYPE: RNA
<213> ORGANISM: Artificial
<220> FEATURE:
<223> OTHER INFORMATION: synthetic

<400> SEQUENCE: 20
uauagagaga gagagaagcu u                                              21

<210> SEQ ID NO 21
<211> LENGTH: 21
<212> TYPE: RNA
<213> ORGANISM: Artificial
<220> FEATURE:
<223> OTHER INFORMATION: synthetic

<400> SEQUENCE: 21
gaggucacug ucaaccagau u                                              21

<210> SEQ ID NO 22
<211> LENGTH: 21
<212> TYPE: RNA
<213> ORGANISM: Artificial
<220> FEATURE:
<223> OTHER INFORMATION: synthetic

<400> SEQUENCE: 22
ucugguugac agugaccucu u                                              21

<210> SEQ ID NO 23
<211> LENGTH: 21
<212> TYPE: RNA
<213> ORGANISM: Artificial
<220> FEATURE:
<223> OTHER INFORMATION: synthetic

<400> SEQUENCE: 23
gccaaggcag acacucuuau u                                              21

<210> SEQ ID NO 24
<211> LENGTH: 21
<212> TYPE: RNA
<213> ORGANISM: Artificial
<220> FEATURE:
<223> OTHER INFORMATION: synthetic

<400> SEQUENCE: 24
uaagaguguc ugccuuggcu u                                              21

<210> SEQ ID NO 25
<211> LENGTH: 21
<212> TYPE: RNA
<213> ORGANISM: Artificial
<220> FEATURE:
<223> OTHER INFORMATION: synthetic

<400> SEQUENCE: 25
ggcagacacu cuuacagauu u                                              21

<210> SEQ ID NO 26
<211> LENGTH: 21
<212> TYPE: RNA
<213> ORGANISM: Artificial
<220> FEATURE:
<223> OTHER INFORMATION: synthetic
```

-continued

<400> SEQUENCE: 26
aucuguaaga gugucugccu u                                      21

<210> SEQ ID NO 27
<211> LENGTH: 21
<212> TYPE: RNA
<213> ORGANISM: Artificial
<220> FEATURE:
<223> OTHER INFORMATION: synthetic

<400> SEQUENCE: 27
uaugaggaga uugcucagau u                                      21

<210> SEQ ID NO 28
<211> LENGTH: 21
<212> TYPE: RNA
<213> ORGANISM: Artificial
<220> FEATURE:
<223> OTHER INFORMATION: synthetic

<400> SEQUENCE: 28
ucugagcaau cuccucauau u                                      21

<210> SEQ ID NO 29
<211> LENGTH: 21
<212> TYPE: RNA
<213> ORGANISM: Artificial
<220> FEATURE:
<223> OTHER INFORMATION: synthetic

<400> SEQUENCE: 29
gucaacaucu cuguagugcu u                                      21

<210> SEQ ID NO 30
<211> LENGTH: 21
<212> TYPE: RNA
<213> ORGANISM: Artificial
<220> FEATURE:
<223> OTHER INFORMATION: synthetic

<400> SEQUENCE: 30
gcacuacaga gauguugacu u                                      21

<210> SEQ ID NO 31
<211> LENGTH: 21
<212> TYPE: RNA
<213> ORGANISM: Artificial
<220> FEATURE:
<223> OTHER INFORMATION: synthetic

<400> SEQUENCE: 31
caucucugua gugcaguccu u                                      21

<210> SEQ ID NO 32
<211> LENGTH: 21
<212> TYPE: RNA
<213> ORGANISM: Artificial
<220> FEATURE:
<223> OTHER INFORMATION: synthetic

<400> SEQUENCE: 32
ggacugcacu acagagaugu u                                      21

```
<210> SEQ ID NO 33
<211> LENGTH: 21
<212> TYPE: RNA
<213> ORGANISM: Artificial
<220> FEATURE:
<223> OTHER INFORMATION: synthetic

<400> SEQUENCE: 33
uaccuguucc acugagcucu u                                              21

<210> SEQ ID NO 34
<211> LENGTH: 21
<212> TYPE: RNA
<213> ORGANISM: Artificial
<220> FEATURE:
<223> OTHER INFORMATION: synthetic

<400> SEQUENCE: 34
gagcucagug gaacagguau u                                              21

<210> SEQ ID NO 35
<211> LENGTH: 21
<212> TYPE: RNA
<213> ORGANISM: Artificial
<220> FEATURE:
<223> OTHER INFORMATION: synthetic

<400> SEQUENCE: 35
caguuaucag cacucagacu u                                              21

<210> SEQ ID NO 36
<211> LENGTH: 21
<212> TYPE: RNA
<213> ORGANISM: Artificial
<220> FEATURE:
<223> OTHER INFORMATION: synthetic

<400> SEQUENCE: 36
gucugagugc ugauaacugu u                                              21

<210> SEQ ID NO 37
<211> LENGTH: 21
<212> TYPE: RNA
<213> ORGANISM: Artificial
<220> FEATURE:
<223> OTHER INFORMATION: synthetic

<400> SEQUENCE: 37
gucaguuguc cugaucuucu u                                              21

<210> SEQ ID NO 38
<211> LENGTH: 21
<212> TYPE: RNA
<213> ORGANISM: Artificial
<220> FEATURE:
<223> OTHER INFORMATION: synthetic

<400> SEQUENCE: 38
gaagaucagg acaacugacu u                                              21

<210> SEQ ID NO 39
<211> LENGTH: 21
<212> TYPE: RNA
<213> ORGANISM: Artificial
<220> FEATURE:
<223> OTHER INFORMATION: synthetic
```

-continued

```
<400> SEQUENCE: 39
gugauguacc uucugaugcu u                                              21

<210> SEQ ID NO 40
<211> LENGTH: 21
<212> TYPE: RNA
<213> ORGANISM: Artificial
<220> FEATURE:
<223> OTHER INFORMATION: synthetic

<400> SEQUENCE: 40
gcaucagaag guacaucacu u                                              21

<210> SEQ ID NO 41
<211> LENGTH: 21
<212> TYPE: RNA
<213> ORGANISM: Artificial
<220> FEATURE:
<223> OTHER INFORMATION: synthetic

<400> SEQUENCE: 41
cugcucacuc gcucaccucu u                                              21

<210> SEQ ID NO 42
<211> LENGTH: 21
<212> TYPE: RNA
<213> ORGANISM: Artificial
<220> FEATURE:
<223> OTHER INFORMATION: synthetic

<400> SEQUENCE: 42
gaggugagcg agugagcagu u                                              21

<210> SEQ ID NO 43
<211> LENGTH: 21
<212> TYPE: RNA
<213> ORGANISM: Artificial
<220> FEATURE:
<223> OTHER INFORMATION: synthetic

<400> SEQUENCE: 43
caagaucauu gcggccaccu u                                              21

<210> SEQ ID NO 44
<211> LENGTH: 21
<212> TYPE: RNA
<213> ORGANISM: Artificial
<220> FEATURE:
<223> OTHER INFORMATION: synthetic

<400> SEQUENCE: 44
gguggccgca augaucuugu u                                              21

<210> SEQ ID NO 45
<211> LENGTH: 21
<212> TYPE: RNA
<213> ORGANISM: Artificial
<220> FEATURE:
<223> OTHER INFORMATION: synthetic

<400> SEQUENCE: 45
guaugagcac gaacuggccu u                                              21
```

<210> SEQ ID NO 46
<211> LENGTH: 21
<212> TYPE: RNA
<213> ORGANISM: Artificial
<220> FEATURE:
<223> OTHER INFORMATION: synthetic

<400> SEQUENCE: 46
ggccaguucg ugcucauacu u                                              21

<210> SEQ ID NO 47
<211> LENGTH: 21
<212> TYPE: RNA
<213> ORGANISM: Artificial
<220> FEATURE:
<223> OTHER INFORMATION: synthetic

<400> SEQUENCE: 47
cguggagaug gaugcugcau u                                              21

<210> SEQ ID NO 48
<211> LENGTH: 21
<212> TYPE: RNA
<213> ORGANISM: Artificial
<220> FEATURE:
<223> OTHER INFORMATION: synthetic

<400> SEQUENCE: 48
ugcagcaucc aucuccacgu u                                              21

<210> SEQ ID NO 49
<211> LENGTH: 21
<212> TYPE: RNA
<213> ORGANISM: Artificial
<220> FEATURE:
<223> OTHER INFORMATION: synthetic

<400> SEQUENCE: 49
ugagaugcgu gaccaguacu u                                              21

<210> SEQ ID NO 50
<211> LENGTH: 21
<212> TYPE: RNA
<213> ORGANISM: Artificial
<220> FEATURE:
<223> OTHER INFORMATION: synthetic

<400> SEQUENCE: 50
guacugguca cgcaucucau u                                              21

<210> SEQ ID NO 51
<211> LENGTH: 21
<212> TYPE: RNA
<213> ORGANISM: Artificial
<220> FEATURE:
<223> OTHER INFORMATION: synthetic

<400> SEQUENCE: 51
accgcagaga cgcugagacu u                                              21

<210> SEQ ID NO 52
<211> LENGTH: 21
<212> TYPE: RNA
<213> ORGANISM: Artificial
<220> FEATURE:
<223> OTHER INFORMATION: synthetic

<400> SEQUENCE: 52
gucucagcgu cucugcgguu u                                        21

<210> SEQ ID NO 53
<211> LENGTH: 21
<212> TYPE: RNA
<213> ORGANISM: Artificial
<220> FEATURE:
<223> OTHER INFORMATION: synthetic

<400> SEQUENCE: 53
guggccucca acagcgaacu u                                        21

<210> SEQ ID NO 54
<211> LENGTH: 21
<212> TYPE: RNA
<213> ORGANISM: Artificial
<220> FEATURE:
<223> OTHER INFORMATION: synthetic

<400> SEQUENCE: 54
guucgcuguu ggaggccacu u                                        21

<210> SEQ ID NO 55
<211> LENGTH: 21
<212> TYPE: RNA
<213> ORGANISM: Artificial
<220> FEATURE:
<223> OTHER INFORMATION: synthetic

<400> SEQUENCE: 55
cagcgaacug guacagagcu u                                        21

<210> SEQ ID NO 56
<211> LENGTH: 21
<212> TYPE: RNA
<213> ORGANISM: Artificial
<220> FEATURE:
<223> OTHER INFORMATION: synthetic

<400> SEQUENCE: 56
gcucuguacc aguucgcugu u                                        21

<210> SEQ ID NO 57
<211> LENGTH: 21
<212> TYPE: RNA
<213> ORGANISM: Artificial
<220> FEATURE:
<223> OTHER INFORMATION: synthetic

<400> SEQUENCE: 57
ggagcagagc ucauccagcu u                                        21

<210> SEQ ID NO 58
<211> LENGTH: 21
<212> TYPE: RNA
<213> ORGANISM: Artificial
<220> FEATURE:
<223> OTHER INFORMATION: synthetic

<400> SEQUENCE: 58
gcuggaugag cucugcuccu u                                        21

-continued

<210> SEQ ID NO 59
<211> LENGTH: 21
<212> TYPE: RNA
<213> ORGANISM: Artificial
<220> FEATURE:
<223> OTHER INFORMATION: synthetic

<400> SEQUENCE: 59
cugagcugcc ucuaccacau u                                              21

<210> SEQ ID NO 60
<211> LENGTH: 21
<212> TYPE: RNA
<213> ORGANISM: Artificial
<220> FEATURE:
<223> OTHER INFORMATION: synthetic

<400> SEQUENCE: 60
ugugguagag gcagcucagu u                                              21

<210> SEQ ID NO 61
<211> LENGTH: 21
<212> TYPE: RNA
<213> ORGANISM: Artificial
<220> FEATURE:
<223> OTHER INFORMATION: synthetic

<400> SEQUENCE: 61
ggccaccaug cagaaccucu u                                              21

<210> SEQ ID NO 62
<211> LENGTH: 21
<212> TYPE: RNA
<213> ORGANISM: Artificial
<220> FEATURE:
<223> OTHER INFORMATION: synthetic

<400> SEQUENCE: 62
gagguucugc augguggccu u                                              21

<210> SEQ ID NO 63
<211> LENGTH: 21
<212> TYPE: RNA
<213> ORGANISM: Artificial
<220> FEATURE:
<223> OTHER INFORMATION: synthetic

<400> SEQUENCE: 63
cacugagcug gaggugaagu u                                              21

<210> SEQ ID NO 64
<211> LENGTH: 21
<212> TYPE: RNA
<213> ORGANISM: Artificial
<220> FEATURE:
<223> OTHER INFORMATION: synthetic

<400> SEQUENCE: 64
cuucaccucc agcucagugu u                                              21

<210> SEQ ID NO 65
<211> LENGTH: 21
<212> TYPE: RNA
<213> ORGANISM: Artificial
<220> FEATURE:
<223> OTHER INFORMATION: synthetic

```
<400> SEQUENCE: 65
gauccgugac ugguaccagu u                                              21

<210> SEQ ID NO 66
<211> LENGTH: 21
<212> TYPE: RNA
<213> ORGANISM: Artificial
<220> FEATURE:
<223> OTHER INFORMATION: synthetic

<400> SEQUENCE: 66
cugguaccag ucacggaucu u                                              21

<210> SEQ ID NO 67
<211> LENGTH: 21
<212> TYPE: RNA
<213> ORGANISM: Artificial
<220> FEATURE:
<223> OTHER INFORMATION: synthetic

<400> SEQUENCE: 67
uugaggagcu gcagaacaau u                                              21

<210> SEQ ID NO 68
<211> LENGTH: 21
<212> TYPE: RNA
<213> ORGANISM: Artificial
<220> FEATURE:
<223> OTHER INFORMATION: synthetic

<400> SEQUENCE: 68
uuguucugca gcuccucaau u                                              21

<210> SEQ ID NO 69
<211> LENGTH: 21
<212> TYPE: RNA
<213> ORGANISM: Artificial
<220> FEATURE:
<223> OTHER INFORMATION: synthetic

<400> SEQUENCE: 69
caagauccuc acagccaccu u                                              21

<210> SEQ ID NO 70
<211> LENGTH: 21
<212> TYPE: RNA
<213> ORGANISM: Artificial
<220> FEATURE:
<223> OTHER INFORMATION: synthetic

<400> SEQUENCE: 70
gguggcugug aggaucuugu u                                              21

<210> SEQ ID NO 71
<211> LENGTH: 21
<212> TYPE: RNA
<213> ORGANISM: Artificial
<220> FEATURE:
<223> OTHER INFORMATION: synthetic

<400> SEQUENCE: 71
gauccucaca gccaccgugu u                                              21
```

-continued

<210> SEQ ID NO 72
<211> LENGTH: 21
<212> TYPE: RNA
<213> ORGANISM: Artificial
<220> FEATURE:
<223> OTHER INFORMATION: synthetic

<400> SEQUENCE: 72
cacgguggcu gugaggaucu u                                              21

<210> SEQ ID NO 73
<211> LENGTH: 21
<212> TYPE: RNA
<213> ORGANISM: Artificial
<220> FEATURE:
<223> OTHER INFORMATION: synthetic

<400> SEQUENCE: 73
ugccaacauc cugcuacagu u                                              21

<210> SEQ ID NO 74
<211> LENGTH: 21
<212> TYPE: RNA
<213> ORGANISM: Artificial
<220> FEATURE:
<223> OTHER INFORMATION: synthetic

<400> SEQUENCE: 74
cuguagcagg auguuggcau u                                              21

<210> SEQ ID NO 75
<211> LENGTH: 21
<212> TYPE: RNA
<213> ORGANISM: Artificial
<220> FEATURE:
<223> OTHER INFORMATION: synthetic

<400> SEQUENCE: 75
cauccugcua cagauugacu u                                              21

<210> SEQ ID NO 76
<211> LENGTH: 21
<212> TYPE: RNA
<213> ORGANISM: Artificial
<220> FEATURE:
<223> OTHER INFORMATION: synthetic

<400> SEQUENCE: 76
gucaaucugu agcaggaugu u                                              21

<210> SEQ ID NO 77
<211> LENGTH: 21
<212> TYPE: RNA
<213> ORGANISM: Artificial
<220> FEATURE:
<223> OTHER INFORMATION: synthetic

<400> SEQUENCE: 77
gaagaaccac gaggaggagu u                                              21

<210> SEQ ID NO 78
<211> LENGTH: 21
<212> TYPE: RNA
<213> ORGANISM: Artificial
<220> FEATURE:
<223> OTHER INFORMATION: synthetic

```
<400> SEQUENCE: 78
gaagaaccac gaggaggagu u                                              21

<210> SEQ ID NO 79
<211> LENGTH: 21
<212> TYPE: RNA
<213> ORGANISM: Artificial
<220> FEATURE:
<223> OTHER INFORMATION: synthetic

<400> SEQUENCE: 79
gaagaaccac gaggaggagu u                                              21

<210> SEQ ID NO 80
<211> LENGTH: 21
<212> TYPE: RNA
<213> ORGANISM: Artificial
<220> FEATURE:
<223> OTHER INFORMATION: synthetic

<400> SEQUENCE: 80
caucuccucc ucgugguucu u                                              21

<210> SEQ ID NO 81
<211> LENGTH: 47
<212> TYPE: DNA
<213> ORGANISM: Artificial
<220> FEATURE:
<223> OTHER INFORMATION: synthetic

<400> SEQUENCE: 81
cgtgaacaga tcaagaccct caacaacaag tttgcctcct tcatcga                  47

<210> SEQ ID NO 82
<211> LENGTH: 47
<212> TYPE: DNA
<213> ORGANISM: Artificial
<220> FEATURE:
<223> OTHER INFORMATION: synthetic

<400> SEQUENCE: 82
cgtgaacaga tcaagaccct caaaaacaag tttgcctcct tcatcga                  47

<210> SEQ ID NO 83
<211> LENGTH: 21
<212> TYPE: RNA
<213> ORGANISM: Artificial
<220> FEATURE:
<223> OTHER INFORMATION: synthetic

<400> SEQUENCE: 83
acagaucaag acccucaacu u                                              21

<210> SEQ ID NO 84
<211> LENGTH: 21
<212> TYPE: RNA
<213> ORGANISM: Artificial
<220> FEATURE:
<223> OTHER INFORMATION: synthetic

<400> SEQUENCE: 84
cagaucaaga cccucaacau u                                              21
```

```
<210> SEQ ID NO 85
<211> LENGTH: 21
<212> TYPE: RNA
<213> ORGANISM: Artificial
<220> FEATURE:
<223> OTHER INFORMATION: synthetic

<400> SEQUENCE: 85
agaucaagac ccucaacaau u                                              21

<210> SEQ ID NO 86
<211> LENGTH: 21
<212> TYPE: RNA
<213> ORGANISM: Artificial
<220> FEATURE:
<223> OTHER INFORMATION: synthetic

<400> SEQUENCE: 86
gaucaagacc cucaacaacu u                                              21

<210> SEQ ID NO 87
<211> LENGTH: 21
<212> TYPE: RNA
<213> ORGANISM: Artificial
<220> FEATURE:
<223> OTHER INFORMATION: synthetic

<400> SEQUENCE: 87
aucaagaccc ucaacaacau u                                              21

<210> SEQ ID NO 88
<211> LENGTH: 21
<212> TYPE: RNA
<213> ORGANISM: Artificial
<220> FEATURE:
<223> OTHER INFORMATION: synthetic

<400> SEQUENCE: 88
ucaagacccu caacaacaau u                                              21

<210> SEQ ID NO 89
<211> LENGTH: 21
<212> TYPE: RNA
<213> ORGANISM: Artificial
<220> FEATURE:
<223> OTHER INFORMATION: synthetic

<400> SEQUENCE: 89
caagacccuc aacaacaagu u                                              21

<210> SEQ ID NO 90
<211> LENGTH: 21
<212> TYPE: RNA
<213> ORGANISM: Artificial
<220> FEATURE:
<223> OTHER INFORMATION: synthetic

<400> SEQUENCE: 90
aagacccuca acaacaaguu u                                              21

<210> SEQ ID NO 91
<211> LENGTH: 21
<212> TYPE: RNA
<213> ORGANISM: Artificial
<220> FEATURE:
<223> OTHER INFORMATION: synthetic
```

```
<400> SEQUENCE: 91
agacccucaa caacaaguuu u                                              21

<210> SEQ ID NO 92
<211> LENGTH: 21
<212> TYPE: RNA
<213> ORGANISM: Artificial
<220> FEATURE:
<223> OTHER INFORMATION: synthetic

<400> SEQUENCE: 92
gacccucaac aacaaguuuu u                                              21

<210> SEQ ID NO 93
<211> LENGTH: 21
<212> TYPE: RNA
<213> ORGANISM: Artificial
<220> FEATURE:
<223> OTHER INFORMATION: synthetic

<400> SEQUENCE: 93
acccucaaca acaaguuugu u                                              21

<210> SEQ ID NO 94
<211> LENGTH: 21
<212> TYPE: RNA
<213> ORGANISM: Artificial
<220> FEATURE:
<223> OTHER INFORMATION: synthetic

<400> SEQUENCE: 94
cccucaacaa caaguuugcu u                                              21

<210> SEQ ID NO 95
<211> LENGTH: 21
<212> TYPE: RNA
<213> ORGANISM: Artificial
<220> FEATURE:
<223> OTHER INFORMATION: synthetic

<400> SEQUENCE: 95
ccucaacaac aaguuugccu u                                              21

<210> SEQ ID NO 96
<211> LENGTH: 21
<212> TYPE: RNA
<213> ORGANISM: Artificial
<220> FEATURE:
<223> OTHER INFORMATION: synthetic

<400> SEQUENCE: 96
cucaacaaca aguuugccuu u                                              21

<210> SEQ ID NO 97
<211> LENGTH: 21
<212> TYPE: RNA
<213> ORGANISM: Artificial
<220> FEATURE:
<223> OTHER INFORMATION: synthetic

<400> SEQUENCE: 97
ucaacaacaa guuugccucu u                                              21
```

```
<210> SEQ ID NO 98
<211> LENGTH: 21
<212> TYPE: RNA
<213> ORGANISM: Artificial
<220> FEATURE:
<223> OTHER INFORMATION: synthetic

<400> SEQUENCE: 98
caacaacaag uuugccuccu u                                              21

<210> SEQ ID NO 99
<211> LENGTH: 21
<212> TYPE: RNA
<213> ORGANISM: Artificial
<220> FEATURE:
<223> OTHER INFORMATION: synthetic

<400> SEQUENCE: 99
aacaacaagu uugccuccuu u                                              21

<210> SEQ ID NO 100
<211> LENGTH: 21
<212> TYPE: RNA
<213> ORGANISM: Artificial
<220> FEATURE:
<223> OTHER INFORMATION: synthetic

<400> SEQUENCE: 100
acaacaaguu ugccuccuuu u                                              21

<210> SEQ ID NO 101
<211> LENGTH: 21
<212> TYPE: RNA
<213> ORGANISM: Artificial
<220> FEATURE:
<223> OTHER INFORMATION: synthetic

<400> SEQUENCE: 101
caacaaguuu gccuccuucu u                                              21

<210> SEQ ID NO 102
<211> LENGTH: 21
<212> TYPE: RNA
<213> ORGANISM: Artificial
<220> FEATURE:
<223> OTHER INFORMATION: synthetic

<400> SEQUENCE: 102
gaucaagacc cucaaaaacu u                                              21

<210> SEQ ID NO 103
<211> LENGTH: 21
<212> TYPE: RNA
<213> ORGANISM: Artificial
<220> FEATURE:
<223> OTHER INFORMATION: synthetic

<400> SEQUENCE: 103
gaucaagacc cucaacaacu u                                              21

<210> SEQ ID NO 104
<211> LENGTH: 21
<212> TYPE: RNA
<213> ORGANISM: Artificial
<220> FEATURE:
<223> OTHER INFORMATION: synthetic
```

<400> SEQUENCE: 104
gaucaagacc cucaagaacu u                                              21

<210> SEQ ID NO 105
<211> LENGTH: 21
<212> TYPE: RNA
<213> ORGANISM: Artificial
<220> FEATURE:
<223> OTHER INFORMATION: synthetic

<400> SEQUENCE: 105
gaucaagacc cucaauaacu u                                              21

<210> SEQ ID NO 106
<211> LENGTH: 21
<212> TYPE: RNA
<213> ORGANISM: Artificial
<220> FEATURE:
<223> OTHER INFORMATION: synthetic

<400> SEQUENCE: 106
cccucaaaaa caaguuugcu u                                              21

<210> SEQ ID NO 107
<211> LENGTH: 21
<212> TYPE: RNA
<213> ORGANISM: Artificial
<220> FEATURE:
<223> OTHER INFORMATION: synthetic

<400> SEQUENCE: 107
cccucaacaa caaguuugcu u                                              21

<210> SEQ ID NO 108
<211> LENGTH: 21
<212> TYPE: RNA
<213> ORGANISM: Artificial
<220> FEATURE:
<223> OTHER INFORMATION: synthetic

<400> SEQUENCE: 108
cccucaagaa caaguuugcu u                                              21

<210> SEQ ID NO 109
<211> LENGTH: 21
<212> TYPE: RNA
<213> ORGANISM: Artificial
<220> FEATURE:
<223> OTHER INFORMATION: synthetic

<400> SEQUENCE: 109
cccucaauaa caaguuugcu u                                              21

<210> SEQ ID NO 110
<211> LENGTH: 33
<212> TYPE: DNA
<213> ORGANISM: Artificial
<220> FEATURE:
<223> OTHER INFORMATION: synthetic

<400> SEQUENCE: 110
aacagatcaa gaccctcaac aacaagtttg cct                                 33

```
-continued
<210> SEQ ID NO 111
<211> LENGTH: 33
<212> TYPE: DNA
<213> ORGANISM: Artificial
<220> FEATURE:
<223> OTHER INFORMATION: synthetic

<400> SEQUENCE: 111
aacagatcaa gaccctcaaa aacaagtttg cct                                      33
```

METHODS AND COMPOSITIONS FOR TREATING KERATIN HYPERPROLIFERATIVE DISORDERS

FIELD OF THE INVENTION

The present invention is related generally to methods and compositions for treating cutaneous disorders of epidermal hyperproliferation including: calluses, corns, keratosis pilaris (KP), psoriasis, and other less common conditions such as keratosis follicularis, pityriasis rubra pilaris, Clouston syndrome, and other palmoplantar keratodermas. More particularly, the present invention is related to the use of RNAi and in particular transdermally-administered siRNA or shRNA to treat calluses, corns (clavi) and KP.

BACKGROUND OF THE INVENTION

Disorders that result in hyperproliferation of the epidermis such as corns, calluses, keratosis pilaris, psoriasis, and other less common conditions, account for a large percentage of skin disease worldwide. A commonality among these disorders is that friction and/or pressure typically precipitate or worsen the clinical manifestations of the disease. The shared molecular feature among these disorders of hyperproliferation is expression of a panel of keratins (the hyperproliferation keratins, K6, K16, and K17).

Keratosis pilaris is a very common, benign skin condition in which keratin protein in the skin forms hard plugs within hair follicles and often lessens or disappears with age. KP consists of a clustering of small, usually 1-2 mm, flesh-colored to slightly erythematous follicular bumps commonly found on the backs of the upper arms. The texture is frequently very coarse due to protrusion of the keratin plugs from the hair follicles. KP may also appear on the buttocks and thighs, where it may be precipitated or worsened by friction from clothing. Less commonly, KP can be seen on the face, where it is termed KP atrophicans faciei. Histologically, these lesions demonstrate keratin plugging of the hair follicles. The condition is generally worse in winter and may improve in the summer. It is associated with atopic dermatitis (eczema) and is hereditary, but the genetic basis of the disease is unknown.

Indeed, the underlying genetic cause of corns, calluses, and psoriasis also remains unknown, but they are similarly caused by friction and pressure generated between the foot and footwear. Histologically, these lesions show a thickened stratum corneum and over time, they develop a central keratin plug that presses painfully into the dermis. The shared pathophysiology involved in the development of corns, calluses, and KP lesions likely explains the shared overexpression of the hyperproliferative keratins.

Psoriasis, although not considered to be a classic disorder of keratinization, also shows overexpression of the hyperproliferative keratins, primarily K16 and K17. In addition, psoriatic lesions tend to develop or extend into areas of trauma, where these same keratins are activated (a symptom referred to as Koebnerization).

Although good emollients or topical treatment with keratolytic agents such as urea, lactic acid, Retin A (tretinoin), or vitamin D analogs may soften and soothe the symptoms of epidermal proliferation, there is currently no medication that eliminates the disease manifestations. Available treatments are directed at symptomatic manifestations of the disorders but generally do not affect the underlying cause as it has heretofore been unknown. As individual patients are generally troubled by different manifestations of the disease, no single treatment plan is known to be effective for treating the hyperproliferation as a whole. Treatment options for epidermal hyperproliferation fall into several broad categories, non-invasive (mechanical), invasive (surgical), chemical, and pharmacological. Currently no treatment options are available for corns, calluses or KP, which address the underlying cause of the disorder and therefore prevent the occurrence of symptoms.

SUMMARY OF THE INVENTION

As such it would be advantageous to develop a method of treatment for corns, calluses, and/or KP, which prevented or suppressed the occurrence of the symptoms. The present invention provides methods and compositions for treating or preventing the manifestation of disorders of keratin hyperproliferation, including primarily corns, calluses, psoriasis and keratosis pilaris. In one embodiment a method of treating or preventing hyperproliferation skin disorders includes administering a therapeutically effective amount of an RNA sequence which inhibits expression of a gene encoding for a keratin selected from the group consisting of K6a, K6b, K16, K17, and combinations thereof.

In addition to the foregoing, the present invention encompasses formulations for administering the RNA sequences recited herein to target cells of a subject. Examples of such formulations include without limitation, topical formulations, including gels, lotions, crèmes, ointments, adhesives, and pastes, as well as transdermal patches, intradermal injections (including needle arrays and "dissolvable" needles), iontophoretic mechanisms, electroporation, sonophoresis, etc.

Reference will now be made to the exemplary embodiments of the present invention, and specific language will be used herein to describe the same. It will nevertheless be understood that no limitation of the scope of the invention is thereby intended.

BRIEF DESCRIPTION OF THE DRAWINGS

FIG. 1 shows comparative histology and immunostaining for keratins including K6, K16 and K17 from patient KP biopsies as well as biopsies from eccrine glands as controls (FIG. 1D). The immunostained KP sections show strong expression of the "inducible keratins" including K6, K16 and K17. Three separate patient biopsies of KP on the upper outer arms are shown (FIG. 1A, FIG. 1B, and FIG. 1C). Each of these lesions demonstrates the typical keratin plugging of the follicular structures. Immunostaining with anti-K6, -K16, and -K17 shows expression of the hyperproliferative keratins relative to a negative control. Normal follicular structures do not typically demonstrate this level of hyperproliferative keratin expression.

FIG. 3 shows that exact sequence identity is necessary for inhibition of wild type and control K6a expression by siRNAs at positions 4 and 12. A. SiRNAs corresponding to positions 4 and 12 were designed and synthesized to target all possible nucleotides at mRNA position 513. Each siRNA (1 nM final concentration) was co-transfected into 293FT tissue culture cells with 150 ng of either the K6a(WT)/YFP (Panel B) or K6a(control)/YFP (Panel C) expression plasmid and were visualized by fluorescence microscopy using an eGFP filter set. Only the siRNAs with exact sequence identity (WT siRNAs against the WT plasmid and control siRNAs against the control plasmid) showed inhibition of expression, while little or no effect was observed with the non-identical siRNAs, which differ only at nucleotide 513.

DETAILED DESCRIPTION OF THE INVENTION

Figure 2:
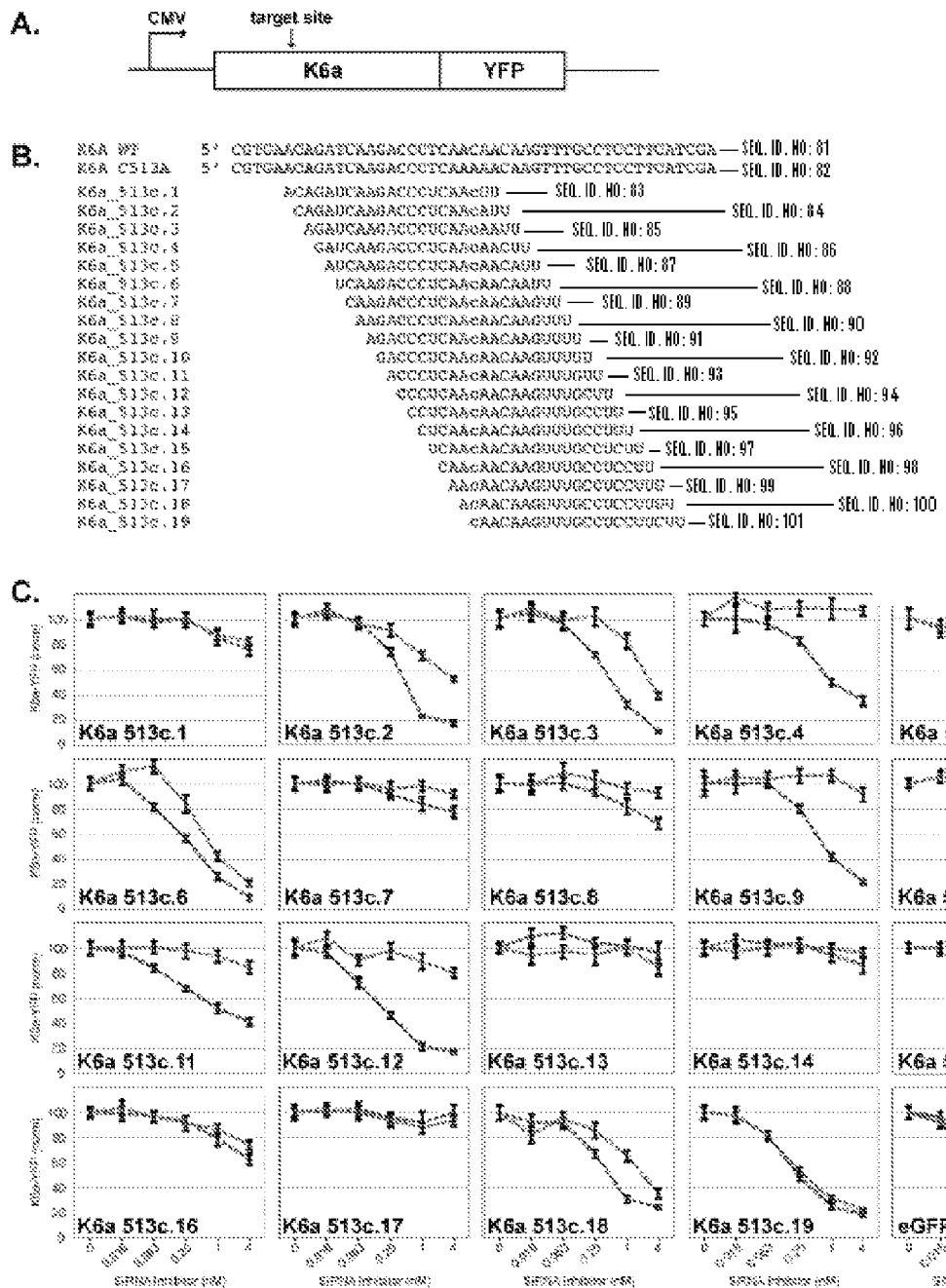
FIG. 2 shows a sequence walk of siRNA inhibitors targeting a specific region of the K6a mRNA (i.e. the region surrounding C513). The fusion bicistronic reporter system is shown in Panel A. Panel B shows the quantitative FACS results of a complete siRNA sequence walk of this specific region of K6a. SiRNAs (19+2 format) were designed and synthesized to screen all possible target sequences containing C513. Each siRNA was co-transfected into 293FT tissue culture cells with either a expression vector encoding a perfectly matched K6a(WT)/YFP fusion target mRNA, or a control mRNA (K6a(control)/YFP) which contains a single nucleotide change (C513A) to demonstrate single-nucleotide specificity (red). 48 hours following transfection, the cells were trypsinized and analyzed for YFP expression using a Becton Dickinson FACScan using channel FL1 (530 nm emission filter). 5,000 cells per transfection were analyzed. The data were generated by gating the cells and determining the percentage of cells that dropped below the gate with and without siRNA treatment. The data were normalized (to 100) and then corrected against cells transfected with NSC4 siRNA (non-specific control from Dharmacon). These results indicate that some siRNAs such as K6a 513c.4 (WT.4) and K6a 513c.12 (WT.12) can strongly discriminate between wildtype K6a and a control K6a that contains a single nucleotide mutation whereas other siRNAs such as K6a 513c.13-17 (WT.13-17) have little or no effect on either.

A new genetic disorder therapy, which is being heavily researched is RNA interference (RNAi). RNAi is an evolutionarily conserved mechanism that results in specific gene inhibition. In the RNAi pathway, double-stranded RNA can effectively induce potent gene silencing without inducing an immune response. RNAi is mediated by RNA-induced silencing complex (RISC), a sequence specific, multi-component nuclease that destroys messenger RNAs homologous to the silencing trigger. RISC is known to contain short RNAs (from 15-31 nucleotides in length), which are derived from double-stranded RNA triggers. A more detailed discussion of the RNAi process in general may be found in *Gene Silencing by RNA Interference: Technology and Application* (Muhammad Sohail ed., 2005), which is incorporated herein by reference.

The present invention illustrates that diseases of the skin with well-described mechanisms are amenable to nucleic acid-based therapies. Although normal skin (and especially the stratum corneum) represents a formidable barrier to topical nucleic acid delivery, a number of methods have been used to successfully deliver nucleic acids to skin. The present invention uses a variety of delivery mechanisms to deliver key RNA inhibitors including intradermal injection and cream formulations.

Although the present invention illustrates the use of RNAi to treat KP, corns or calluses, the ability to locally deliver specific robust siRNA-based gene inhibitors would be a boon to patients suffering from a number of hair follicle skin disorders in addition to KP such as keratosis follicularis, and as such, the general principles embodied herein may be applied for treatment of such conditions.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting.

In describing and claiming the present invention, the following terminology will be used.

The singular forms "a," "an," and "the" include plural referents unless the context clearly dictates otherwise. Thus, for example, reference to "an RNA sequence" includes reference to one or more of such RNA sequences, and reference to "the genetic mutation" includes reference to one or more of such genetic mutation.

As used herein, "subject" refers to a mammal having who currently manifests, has in the past manifested, or is genetically predisposed to the potential manifestation of a hyperkeratotic skin (i.e. keratin hyperproliferation) condition or disorder. In some aspects, such subject may be a human.

The term "gene" refers to a nucleic acid comprising an open reading frame encoding a polypeptide.

The term "sequence" when used with respect to RNA inhibitors refers to at a minimum, a single strand oligonucleotide of between about 15 and 31 base pairs (siRNA), which may hybridize with target mRNA and thereby inhibits the expression of the targeted gene. The sequence may be formed and delivered to a subject as double stranded RNA, the second strand being complimentary to the inhibitory sequence, or as small hairpin RNA (shRNA), the inhibitory sequence being attached through a loop sequence to a sequence complimentary to the inhibitory sequence. The sequence may also include 2 nucleotide overhangs.

As used herein, the terms "target cell" or "target cells", refer to cells that produce keratin proteins, the improper production of which contribute to a keratin hyperproliferation disorder. Such keratins include without limitation, those recited herein.

As used herein, the term "inhibition of" or "silencing of" with respect to genetic expression refers to the absence of, or at least an observable decrease in, the level of protein from a target gene.

As used herein, the term "hyperproliferation skin disorder" refers to disorders of the skin in which there is a hyperproliferation of the keratins K6 (K6a and/or K6b), K16, and/or K17. The hyperproliferation of the keratins can be from caused by any source including but not limited to external factors (e.g. rubbing or pressure of a shoe to form a callus or corn) or internal/biological factors (e.g. over expression of a gene).

The term "expression" with respect to a gene sequence refers to transcription of the gene and, as appropriate, translation of the resulting mRNA transcript to a protein.

"Specificity" refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and flow cytometry (FACS). For RNA-mediated inhibition in a whole organism or cell line, gene expression is conveniently assayed by use of a reporter or drug resistance gene whose protein product is easily assayed. Such reporter genes can include but are not limited to beta galactosidase (LACZ), beta glucoronidase (GUS), chloramphenicol acetyltransferase (CAT), green fluorescent protein (GFP) or other fluorescent proteins (e.g. YFP, BFP, CFP, DsRed, Tomato, etc.), horseradish peroxidase (HRP), luciferase (LUC), etc.

As used herein, "effective amount" or "therapeutically effective amount" of an RNA refers to a sufficient amount of RNA to perform an intended task and achieve an intended result. For example, an effective amount of siRNA may be an amount which is sufficient to silence expression a keratin gene. It is understood that various biological factors may affect the ability of a particular RNA sequence to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine.

As used herein, the term "about" is used to provide flexibility to a numerical range endpoint by providing that a given value may be "a little above" or "a little below" the endpoint.

As used herein, the term "substantially" refers to the complete or nearly complete extent or degree of an action, characteristic, property, state, structure, item, or result.

As used herein, sequences, compounds, formulations, delivery mechanisms, or other items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.5 to 10 g" should be interpreted to include not only the explicitly recited values of about 0.5 g to about 10.0 g, but also include individual values and sub-ranges within the indicated range. Thus, included in this numerical range are individual values such as 2, 5, and 7, and sub-ranges such as from 2 to 8, 4 to 6, etc. This same principle applies to ranges reciting only one numerical value. Furthermore, such an interpretation should apply regardless of the breadth of the range or the characteristics being described.

Unless otherwise defined, all technical and scientific terms used herein have the same meaning as commonly understood to one of ordinary skill in the art to which this invention belongs. Although any methods, devices and materials similar or equivalent to those described herein can be used in the practice or testing of the invention, representative methods, devices, and materials are described below.

As mentioned above, keratosis pilaris is generally a disorder resulting in keratin plugging of hair follicles, and corns and calluses represent a reactive hyperproliferation in response to trauma. Although some of the manifestations of the disease differ by the location of the hyperproliferation (palms and soles versus perifollicular) the general underlying cause of each disorder is generally the same, overexpression of inducible keratin encoding genes. Keratins are the type I and type II intermediate filament proteins, which form a cytoskeletal network within all epithelial cells. Overexpression of these genes is associated with thickened, and abnormally cornified and frequently hyperproliferative epidermis which present clinically as a variety of conditions such as corns, calluses, KP and keratodermas such as PC. The overexpression of four keratin genes may be associated with corns, calluses, and KP, namely K6a, K6b, K16, and K17. The reason for overexpression of these genes is not known, but may involve trauma to the hands or feet or undesirable stimulation of the hair follicles by friction or other manipulation.

The present invention provides methods for treating corns, calluses and KP by administering therapeutically effective amounts of siRNAs that specifically target K6a, K6b, K16 and/or K17 in the subject. The prepared inhibitory sequences can vary in length but generally are from about 15 to 31 bases in length. These prepared sequences are generally considered to be small interfering siRNA (siRNA). The RNA sequences of the present invention can include modifications to either the phosphate-sugar backbone or the base. For example, the phosphodiester linkages of the RNA may be modified to include at least one of a nitrogen or sulfur or other heteroatom. Likewise, bases may be modified to block the activity of nucleases. The RNA sequence may be produced enzymatically or by partial/total organic synthesis; any modified ribonucleotide can be introduced by in vitro enzymatic or organic synthesis. The RNA sequences of the present invention can be administered as hybridized double stranded complementary RNA (dsRNA), as short single-stranded hybridized RNAs (typically siRNA), or alternatively as a single hairpin molecule of RNA (shRNA) that contains a 15 to 31-basepair stem. The desirability of using dsRNA vs. shRNA can vary depending on the particular sequence and the mutation for which inhibition is sought; however, both forms have been shown to be capable and effective for use in gene silencing. For more information on small hairpin RNA see Wang et al., *Molecular Therapy*, Vol. 12, No. 3, September 2005, which is hereby incorporated by reference in its entirety. Whether administered as dsRNA or shRNA, there are a variety of means by which the RNA sequences of the present invention can be delivered to a subject. Suitable delivery mechanisms include but are not limited to injection, including intradermal injection using single needles and needle arrays, topical formulations, such as lotions, creams, gels, ointments, jellies (such as petroleum jelly), adhesives, pastes, liquids, soaps, shampoos, transdermal patches, films, electrophoresis, or combinations thereof. In one aspect, the specific carrier utilized in the production of a formulation may be selected because of its positive impact on skin. For example, carriers that moisturize, hydrate, or otherwise benefit the skin can be used.

In some aspects, the RNA sequences of the present invention can be administered in combination with other therapeutically effective compounds. Ideally, such compounds would be those agents having a therapeutic skin effect, particularly on the manifestations of the disorder being treated. Examples of such compounds include but are not limited to corticosteroidsm, (e.g. hydrocortisone, prednisone, clobetasol propionate, etc.), a lanolin-containing product, aloe vera, urea, propylene glycol, α-hydroxy acids, lactic acid, salicylic acid, vitamin $D_3$ and its derivatives, vitamin A and retinoids, levothyroxin, NSAIDS, cyclosporine, methotrexate sodium, anthralin, acitretin, tazarotene, coal tar, clobetasol propionate, botulinum toxin, topical anesthetics, antihistamine, and combinations thereof.

Effectiveness of the KP inhibition can depend on the particular RNA inhibitor as well as the amount of inhibiting RNA administered to the subject. Other biologically related factors may also be variables in determining the effectiveness of the inhibitors. Therapeutically effective amounts of RNA sequences can be from about 0.1 mg to about 10 mg.

In one embodiment, the present invention provides a method of treating a subject with corns, calluses, and/or KP by administering to the subject an RNA sequence which inhibits the expression of the gene encoding for a keratin selected from the group of K6a, K6b, K16, K17, and combinations thereof. It has been discovered that there is redundancy of keratin expression in keratinocytes, and as such it is possible to suppress expression of wildtype keratins without causing unwanted side-effects. In other words, by simply eliminating production of any one or more of the above-recited keratins it may be possible to reduce or eliminate the symptoms of corns, calluses, and/or KP without any unwanted side effects because other keratins overlap the functions performed by the above-recited keratins. Additionally, due to the relatively small numbers of genes expressed in skin, it is believed that the methods of the present invention can be used effectively with minimal off-target effects.

Non-limiting examples of sequences which can be used to inhibit the expression of the K6a keratin include but are not limited to SEQ. TD NO: 1, SEQ. ID NO: 2, SEQ. ID NO: 3, SEQ. ID NO: 4, SEQ. ID NO: 5, SEQ. ID NO: 6, SEQ. ID NO: 7, SEQ. ID NO: 8, SEQ. ID NO: 9, SEQ. ID NO: 10, SEQ. ID NO: 11, SEQ. ID NO: 12, SEQ. ID NO: 13, SEQ. ID NO: 14, SEQ. ID NO: 15, SEQ. ID NO: 16, SEQ. ID NO: 17, SEQ. ID NO: 18, SEQ. ID NO: 19, SEQ ID NO: 20, SEQ. ID NO: 86, SEQ ID NO: 91, SEQ. ID NO: 92, SEQ. ID NO: 94, and mixtures thereof.

Non-limiting examples of sequences which are effective against the K6b keratin include but are not limited to SEQ. ID NO: 21, SEQ. ID NO: 22, SEQ. ID NO: 23, SEQ. ID NO: 24, SEQ. ID NO: 25, SEQ. ID NO: 26, SEQ. ID NO: 27, SEQ. ID NO: 28, SEQ. ID NO: 29, SEQ ID NO: 30, SEQ. ID NO: 31, SEQ. ID NO: 32, SEQ. ID NO: 33, SEQ. ID NO: 34, SEQ. ID NO: 35, SEQ. ID NO: 36, SEQ. ID NO: 37, SEQ. ID NO: 38, SEQ. ID NO: 39, SEQ. ID NO: 40, and mixtures thereof.

Similarly, non-limiting examples of sequences which are effective against the K16 keratin include but are not limited to SEQ. ID NO: 41, SEQ. ID NO: 42, SEQ. ID NO:43, SEQ. ID NO: 44, SEQ. ID NO: 45, SEQ. ID NO: 46, SEQ. ID NO: 47, SEQ. ID NO: 48, SEQ. ID NO: 49, SEQ. ID NO: 50, SEQ ID NO: 51, SEQ. ID NO: 52, SEQ. ID NO: 53, SEQ. ID NO: 54, SEQ. ID NO: 55, SEQ. ID NO: 56, SEQ. ID NO: 57, SEQ. ID NO: 58, SEQ. ID NO: 59, SEQ. ID NO: 60, and mixtures thereof.

Non-limiting examples of sequences which can be effective in inhibiting K17 keratin include but are not limited to SEQ. ID NO: 61, SEQ. ID NO: 62, SEQ. ID NO: 63, SEQ. ID NO: 64, SEQ. ID NO: 65, SEQ. ID NO: 66, SEQ. ID NO: 67, SEQ. ID NO: 68, SEQ. ID NO: 69, SEQ. ID NO: 70, SEQ. ID NO: 71, SEQ. ID NO: 72, SEQ. ID NO: 73, SEQ. ID NO: 74, SEQ. ID NO: 75, SEQ. ID NO: 76, SEQ. ID NO: 77, SEQ. ID NO: 78, SEQ. ID NO: 79, SEQ. ID NO: 80, and mixtures thereof.

The sequences set forth above are merely exemplary and are not intended to limit the present invention. Other sequences may also be used to inhibit the expression of any of the targeted keratin genes in order to treat the keratin hyperproliferation disorders taught herein. Such sequences could be readily identified and created by one of ordinary skill in the art using the methods and techniques set forth herein as well as others well known in the art.

Methodology

In order to show that hyperproliferative keratin-specific siRNA result in down-regulation of K6a expression, human 293FT cells were transfected with wildtype and mutant (as one control that should be unaffected by treatment—this particular single nucleotide mutation, used as control in these experiments, results in an asparagine to lysine amino acid change, N171K, and is one cause of the rare skin disorder pachyonychia congenita) forms of K6a fused to a reporter protein. In order to differentiate inhibition of wildtype versus mutant genes, a fluorescence-based FACS assay was used. The assay tests siRNA inhibitors against wildtype and mutant gene mRNA in which the target gene is fused to a reporter gene, in this case yellow fluorescent protein (YFP). Once the problematic target gene (e.g. in KP) is identified, siRNA inhibitors can be made that target various regions of the mRNA. Co-transfection experiments of wildtype and target mutation expression constructs reveal which inhibitors potently inhibit the wildtype gene, with little or no effect on mutant expression. As a positive control, an eGFP-specific siRNA inhibitor can be co-transfected with the wildtype and mutant constructs. YFP and eGFP are nearly identical in sequence and there are no nucleotide differences in the target site for the eGFP siRNA inhibitor used. Identified inhibitors can be further tested to check whether endogenous pre-existing keratin expression can be inhibited and evaluate "off-target" effects. Next, the inhibitors can be evaluated in a mouse model in which the siRNA efficacy is tested on K6a targets fused to the reporter gene firefly luciferase (fLuc) and expression monitored by in vivo imaging.

EXAMPLES

Example 1

KP Lesions Express High Levels of K6, K16 and K17 Proteins

An immunostaining assay of three separate patient biopsies taken from patients were utilized to demonstrate that K6, K16, and K17 are overexpressed in KP lesions. Each tissue sample was formalin-fixed, paraffin-embedded, and immunostained with the Dako Envision System (catalog K4007, DakoCytomation, Denmark). The antibodies used were 1:10 dilution of K6 (Progen Biotecknik), a 1:10 dilution of K16 (Lab Vision), and a 1:10 dilution of K17 (Sigma). A 1:400 dilution of 488-conjugated goat anti-mouse secondary antibody was used for all stains. This is a sensitive system that utilizes horseradish peroxidase-conjugated secondary antibodies.

Example 2

Differential Inhibition of Mutant K6a/YFP vs. Wildtype by Mutant-Specific K6a SiRNAs in Tissue Culture Cells A fluorescence-based tissue culture assay was developed and used to test siRNA inhibitors against wildtype and control (to demonstrate single nucleotide specificity) K6a mRNAs in which the target gene is fused to a reporter gene (YFP). SiRNAs designed to target the C513 region of the wildtype K6a gene were tested. A series of siRNA inhibitors (19+2 format) that target every possible sequence surrounding the C513 site were designed and synthesized (supplied by Dharmacon RNA Technologies). FIG. 2 shows the sequence walk of the siRNA inhibitors for the C513 site of K6a, as well as the amount of inhibition against the wildtype and control expression plasmids. Co-transfection experiments with K6a(WT)/YFP and K6a(control)/YFP expression constructs were performed. Each siRNA was co-transfected into 293FT tissue culture cells with a plasmid vector expressing either K6a (WT)/YFP mRNA or a similar construct expressing the K6a (control)/YFP mRNA. 48 hours following transfection, the cells were trypsinized and analyzed for YFP expression using a Becton Dickson FACScan using channel FL1 (530 nm emission filter). Five thousand cells per transfection were analyzed. The data were generated by gating the cells and determining the percentage of cells that dropped below the gate with and without siRNA treatment. As a positive control, eGFP-specific siRNA inhibitors were co-transfected with the wildtype and control K6a/YFP constructs (the 50% inhibitory concentration, $IC_{50}$, values were 0.1 nM against both constructs). No effect was observed with the irrelevant non-specific control (NSC4) siRNA inhibitor. The data were normalized and then corrected against cells transfected with the non-specific control. Specifically, the co-transfection experiments revealed several inhibitors including WT.4 and WT.12 (SEQ ID NOS: 86, 91, 92, and 94) that exhibit strong discrimination between wildtype K6a and mutant K6a targets (e.g. $IC_{50}$ values for WT.12 were ~0.2 nM and >4 nM nM against the wildtype and mutant constructs, respectively as determined by FACS analysis). In order to further demonstrate the single nucleotide specificity of WT.4 and WT.12, additional siRNAs were synthesized containing all possible nts at position 513. FIG. 3 shows that only perfect complementarity (i.e. "c" in passenger siRNA strand, "g" in guide strand) results in inhibition of wildtype K6a expression.

These results show that siRNA inhibitors can have robust, specific and high inhibitory activity against wildtype K6a expression, with little or no effect on control K6a (differing by only one nucleotide) activity. As was expected, some of the designed inhibitors exhibited little or no inhibition against either wildtype or control expression.

Example 3

Figure 4:
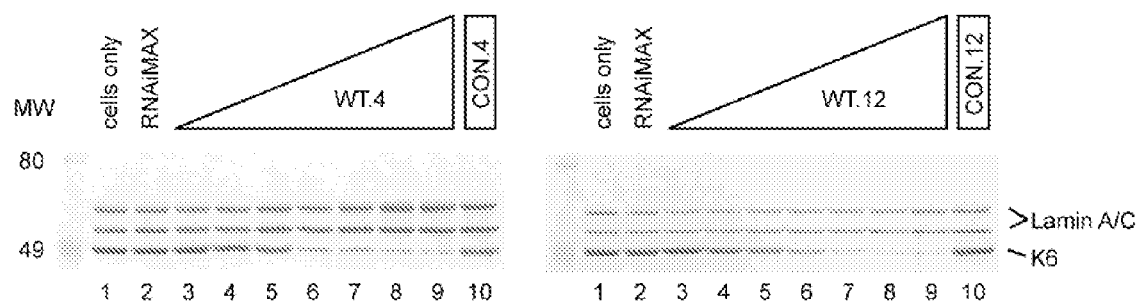
FIG. 4 shows inhibition of endogenous K6 expression in human HaCaT keratinocytes. HaCaT cells were transfected with increasing concentrations of wildtype-specific siRNAs (lanes 3-9 containing 0, 1, 2, 5, 10, 15 and 20 nM WT.4 or WT.12) and as controls 20 nM siRNA that target the single nucleotide change (C513A) (lane 10, CON.4 or CON.12). After 96 hrs, cells were harvested and lysed in SDS-PAGE loading buffer and subjected to denaturing SDS-PAGE analysis and electroblotted to nitrocellulose. K6 expression was detected by specific K6 antibody (Progen) and visualized by the NBT/BCIP system (Promega). The blot was subsequently reacted with an antibody specific to Lamin A/C (Upstate) to show equal lane loading and absence of generalized inhibition resulting from siRNA treatment. These results show that endogenous K6 can be potently down-regulated by siRNAs that also exhibit single-nucleotide specificity.

SiRNA-Mediated Down-Regulation of Pre-Existing K6a Expression in Human Keratinocytes Human HaCaT keratinocytes were transfected with K6a-specific siRNAs (WT.4 and WT.12) to test their ability to inhibit endogenous K6a (FIG. 4). 96 hr post-transfection, cells were lysed and subjected to electrophoresis on a 4-12% bis-tris gel, transferred to nitrocellulose and incubated with a K6-specific antibody (HaCaT cells express K6a but not K6b, unpublished data). A strong band was seen for K6 in untreated HaCaT cells and those treated with the transfection reagent RNAiMAX. In cells treated with either K6a-specific siRNA, WT.4 or WT.12, a dramatic reduction in the amount of K6a protein was observed upon increased concentration of siRNA. No or little effect was observed in cells treated with the control K6a-specific inhibitors, CON.4 or CON.12. The levels of Lamin A/C were unaffected upon addition on K6a-specific siRNA, showing the absence of generalized effects following siRNA treatment. These results indicate that the wildtype K6a siRNAs can inhibit endogenous K6 under conditions where control K6a siRNAs have little or no effect, further demonstrating single nucleotide specificity.

Example 4

Delivery and Effectiveness of SiRNA Inhibitors in Mouse Footpad Keratinocytes

Figure 5:
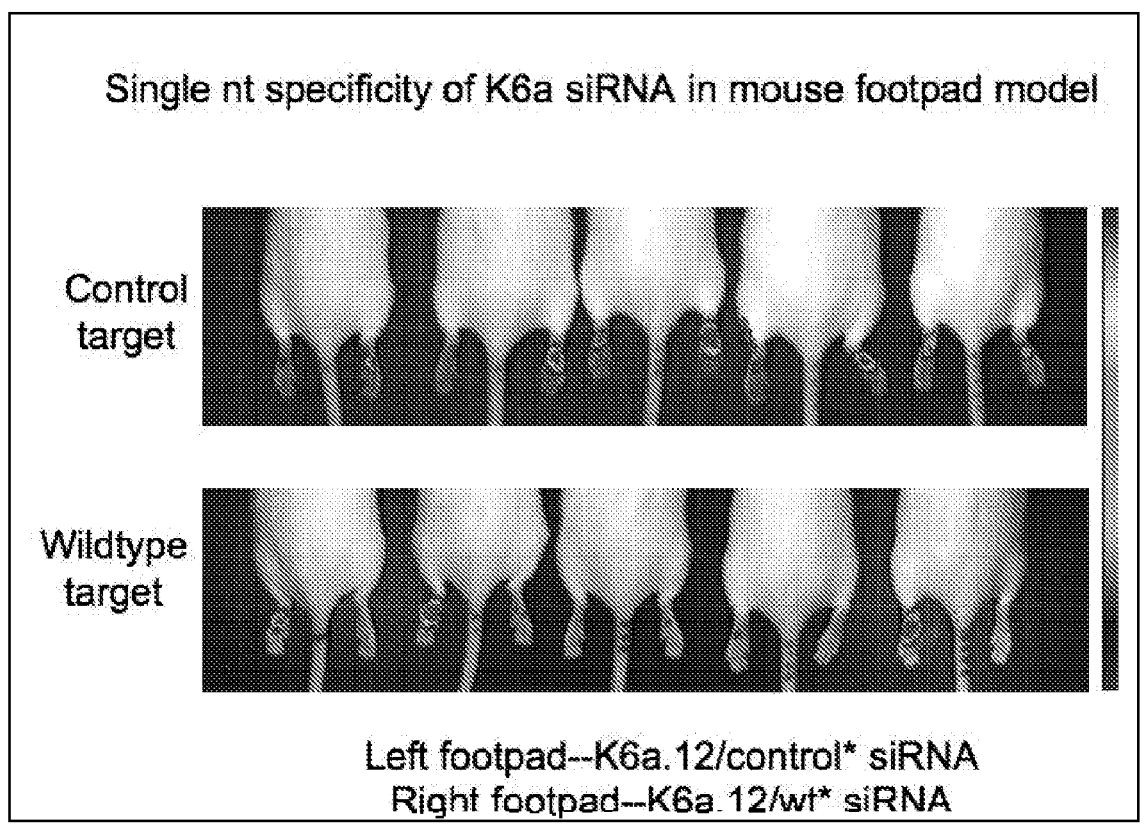
FIG. 5 shows inhibition of K6a(wildtype)/fLuc gene expression by specific siRNAs in a mouse footpad skin model. A. Mice (5 per group) were co-injected intradermally with ~10 µg K6a(WT)/fLuc (bottom mouse panel) or K6a (control)/fLuc (top mouse panel) expression plasmid and ~10 µg of either stabilized (siSTABLE™ from Dharmacon) WT.12 siRNA (right paw) or CON.12 siRNA (left paw). After 24 hrs, luciferase expression in the footpads was determined following IP luciferin injection by whole animal imaging using the Xenogen IVIS in vivo imaging system. Red color represents highest luciferase expression, purple lowest. These results show that the WT.12 siRNA can specifically block expression of wildtype K6a expression in a mouse system with little effect on a control target that only differs by a single nucleotide.

Female FVB mouse footpads were intradermally injected with a WT or control version of a firefly luciferase reporter gene/K6a plasmid (pL2K6a(WT) or pL2K6a(control)), encoding a bicistronic mRNA comprised of the firefly luciferase and K6a open reading frames separated by the foot and mouth virus 2A element to allow equal expression of both fLuc and K6a. The noninvasive analyses of gene expression afforded by this approach allows for the repeated monitoring of reporter gene expression over multiple timepoints in the same group of animals, minimizing the number of mice needed while refining the data sets and maximizing the amount of information obtained. The mice were imaged for luciferase expression at multiple timepoints (typically ranging from 12-120 hours) post gene delivery. FIG. 5 shows the image at the 24-hour timepoint (left paw was treated with control K6a siRNA and the right with WT.12 siRNA).

It is to be understood that the above-described methods, formulations, and experimentals are only illustrative of preferred embodiments of the present invention. Numerous modifications and alternative arrangements may be devised by those skilled in the art without departing from the spirit and scope of the present invention and the appended claims are intended to cover such modifications and arrangements.

Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:

1. A method of treating a hyperproliferation skin disorder in a subject who is manifesting a hyperproliferation disorder, comprising:
    administering to the subject who is manifesting a hyperproliferation disorder selected from the group consisting of keratosis pilaris, calluses, corns, psoriasis, keratosis follicularis, pityriasis rubra pilaris, and Clouston syndrome, a therapeutically effective amount of an RNA sequence which inhibits expression of a gene encoding for a keratin selected from the group consisting of K6a, K6b, K16, K17, and combinations thereof, wherein the inhibited gene encodes the K6a keratin and the RNA sequence is a member selected from the group consisting of: SEQ. ID NO: 2, SEQ. ID NO: 4, SEQ. ID NO: 6, SEQ. ID NO: 8, SEQ. ID NO: 10, SEQ. ID NO: 12, SEQ. ID NO: 14, SEQ. ID NO: 16, SEQ. ID NO: 18, SEQ. ID NO: 20, SEQ. ID NO: 86, SEQ. ID NO: 91, SEQ. ID NO: 92, SEQ. ID NO: 94, and combinations thereof.

2. The method of claim 1, wherein the hyperproliferation skin disorder is keratosis pilaris.

3. The method of claim 1, wherein the hyperproliferation skin disorder is a callus.

4. The method of claim 1, wherein the hyperproliferation skin disorder is a corn.

5. The method of claim 1, wherein the RNA sequence is a small interfering RNA.

6. The method of claim 1, wherein the subject's overexpressed gene encodes keratin 6a (K6a).

7. The method of claim 1, wherein the RNA sequence is administered as double stranded RNA.

8. The method of claim 1, wherein the RNA sequence is administered as a short hairpin RNA.

9. The method of claim 1, wherein the RNA sequence has a length of about 15 to about 31 nucleotides.

10. The method of claim 1, wherein the RNA sequence is administered transdermally.

11. The method of claim 10, wherein the transdermal administration includes formulations and processes selected from the group consisting of: a lotion, a cream, a gel, an ointment, a paste, a transdermal patch, a liposome, iontophoresis, electroporation, sonophoresis, or combinations thereof.

12. The method of claim 1, wherein the RNA sequence is administered by intradermal injection.

13. The method of claim 12, wherein the intradermal injection is accomplished using dissolvable needles.

14. The method of claim 1, wherein the RNA sequence is administered in a therapeutically effective amount of from about 0.1 mg to about 10 mg.

15. The method of claim 1, wherein the RNA sequence contains at least one modified nucleotide.

16. The method of claim 1, wherein the RNA sequence is administered in combination with a therapeutically effective amount of a compound selected from the group consisting of corticosteroid, lanolin, aloe vera, urea, propylene glycol, a-hydroxy acids, lactic acid, salicylic acid, vitamin $D_3$ and its derivatives, vitamin A and retinoids, levothyroxin, NSAIDS, cyclosporine, methotrexate sodium, anthralin, acitretin, tazarotene, coal tar, botulinum toxin, topical anesthetics, antihistamine, and combinations thereof.

17. The method of claim 1, wherein the inhibited gene encodes for a mutated keratin.

18. The method of claim 1, wherein the inhibited gene encodes a wildtype keratin.

19. The method of claim 15, wherein the RNA sequence inhibits expression of both mutated and wildtype keratin genes.

20. The method of claim 1, further comprising the step of selecting a subject who manifests a hyperproliferation skin disorder selected from the group consisting of keratosis pilaris, calluses, corns, psoriasis, keratosis follicularis, pityriasis rubra pilaris, and Clouston syndrome.

21. The method of claim 1, wherein the RNA sequence comprises SEQ. ID NO: 94.

* * * * *